(12) United States Patent
Keyes et al.

(10) Patent No.: US 9,805,170 B2
(45) Date of Patent: Oct. 31, 2017

(54) SYSTEM AND METHODS FOR PERFORMING MEDICAL PHYSICS CALCULATIONS

(75) Inventors: Roy William Keyes, Albuquerque, NM (US); Christian Romano, Albuquerque, NM (US); Shuang Luan, Albuquerque, NM (US); Dorian C. Arnold, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 834 days.

(21) Appl. No.: 13/643,844

(22) PCT Filed: Apr. 28, 2011

(86) PCT No.: PCT/US2011/034312
§ 371 (c)(1),
(2), (4) Date: Oct. 26, 2012

(87) PCT Pub. No.: WO2011/139829
PCT Pub. Date: Nov. 10, 2011

(65) Prior Publication Data
US 2013/0054670 A1    Feb. 28, 2013

Related U.S. Application Data

(60) Provisional application No. 61/343,419, filed on Apr. 28, 2010, provisional application No. 61/339,711, filed on Jul. 16, 2010.

(51) Int. Cl.
*G06F 15/16*    (2006.01)
*G06F 19/00*    (2011.01)
*G06F 9/50*    (2006.01)

(52) U.S. Cl.
CPC ...... *G06F 19/3481* (2013.01); *G06F 19/3437* (2013.01); *G06F 9/5083* (2013.01)

(58) Field of Classification Search
CPC .... A61N 5/103; A61N 5/1031; A61N 5/1064; G06F 19/321; G06F 19/3481;
(Continued)

(56) References Cited

U.S. PATENT DOCUMENTS 6,175,761 B1    1/2001  Frandsen et al.
8,245,237 B2 *  8/2012  Tajima ................. G06F 9/4881
                                          709/226
(Continued)

FOREIGN PATENT DOCUMENTS

JP    2004-240541    8/2004

OTHER PUBLICATIONS

Gu X. et al., GPU-based ultrafast dose calculation using a finite size pencil beam model, Physics in Medicine and Biology, 2009, 6287-6297, vol. 54.*

(Continued)

*Primary Examiner* — Joseph E Avellino
*Assistant Examiner* — Patrick Ngankam
(74) *Attorney, Agent, or Firm* — Valauskas Corder LLC

(57) ABSTRACT

A method of calculating radiation fluence and energy deposition distributions on a networked virtual computational cluster is presented. With this method, complex Monte Carlo simulations that require expansive equipment, personnel, and financial resources can be done efficiently and inexpensively by hospitals and clinics requiring radiation therapy dose calculations.

14 Claims, 5 Drawing Sheets

(58) Field of Classification Search
CPC .. G06F 19/3437; G06F 9/5038; G06F 9/5083; G21K 2201/00
USPC .......................... 709/201; 717/106; 702/179
See application file for complete search history.

(56) References Cited

U.S. PATENT DOCUMENTS

2007/0271547 A1* 11/2007 Gulko .................. G06F 8/451 717/106
2009/0112882 A1 4/2009 Maresh et al.

OTHER PUBLICATIONS

Gu X, et al., GPU-based ultra fast dose calculation using a finite pencil beam model, Physics in Medicine and Biology, 2009, 6287-6297, vol. 54 (https://arxiv.org/ftp/arxiv/papers/0908/0908.4417.pdf).*

ICRU Report 16, Linear Energy Transfer (https://epub.ub.uni-muenchen.de/8949/1/8949.pdf), Jun. 1970.*

Gu X et al. "GPU-based ultra-fast dose calculation using a finite size pencil beam model, Physics in Medicine and Biology", 2009 6287-6297, vol. 54 (http://iopscience.iop.org/article/10.1088/0031-9155/54/20/017/pdf).*

ICRU Report "Linear Energy Transfer", Jun. 1970 (https://core.ac.uk/download/pdf/12169706.pdf).*

Agostinelli S., et al., Nuclear Instruments and Methods in Physics Research Section A: Accelerators, Spectrometers, Detectors and Associated Equipment, Elsevier, 2003, 250-303, vol. 506, No. 3. Link: http://www.sciencedirect.com/science/article/B6TJM-48TJFY8-5/2/23ea98096ce11c1be446850c04cfa498.

Allison J., et al., Geant4 Developments and Applications, IEEE Transactions on Nuclear Science, 2006, 270-278, vol. 53, No. 1.

Amazon, Inc., Creating Healthcare Data Applications to Promote HIPAA and HITECH Compliance, 2012, Link: http://aws.amazon.com/security.

Andriole K. P, et al., Cloud Computing: What is it and could it be useful?, American College of Radiology, 2010, 252-254.

Battistoni G., et al., The FLUKA code: description and benchmarking, American Institute of Physics, 2007, 31-49.

Buck I., et al., Brook for GPUs: Stream Computing on Graphincs Hardware, ACM Inc., 2004, 777-786.

Chetty I. J., et al., Report of the AAPM Task Group No. 105: Issues associated with clinical implementation of Monte Carlo-based photon and electron external beam treatment planning, Medical Physics, 2007, 4818-4853, vol. 34, No. 12.

De Greef M., et al.,Accelerated ray tracing for radiotherapy dose calculations on a GPU, Medical Physics, 2009, 4095-4102, vol. 36, No. 9.

Downes P., et al., High-performance computing for Monte Carlo radiotherapy calculations, Philosophical Transactions of The Royal Society A, 2009, 2607-2617, vol. 367.

Ferrari A., et al., FLUKA: A Multi-Particle Transport Code, Italian National Institute for Nuclear Physics (INFN) and European Organization for Nuclear Research (CERN), 2005.

Foster I., et al., Cloud Computing and Grid Computing 360-Degree Compared, Grid Computing Environments Workshop (GCE), 2008, 1-10. Link: http://dx.doi.org/10.1109/GCE.2008.4738445.

Geelen J., Twenty-one experts define cloud computing,Sys-Con Media, 2009, 1-4 Link: http://www.sys-con.com/node/612375.

Giunta G., et al., A GPGPU Transparent Virtualization Component for High Performance Computing Clouds, Springer-Verlag Berlin Heidelberg, 2010, 379-391.

Gomez A., et al., Reomote Radiotherapy Planning: The eIMRT Project, Studies in Health Technology and Informatics, 2006, 330-335, vol. 120, No. 1.

Gomez A., et al., Monte Carlo Verification of IMRT treatment plans on Grid, Studies in Health Technology and Informatics, 2007, 104-114, vol. 106, No. 1.

Gu X., et al., GPU-based ultra-fast dose calculation using a finite size pencil beam model, Physics in Medicine and Biology, 2009, 6287-6297, vol. 54.

Gu X., et al., Implementation and evaluation of various demons deformable image registration algorithms on a GPU, Physics in Medicine and Biology, 2010, 207-219, vol. 55.

Hirayama H., et al., The EGS5 Code System, Radiation Science Center, 2005.

Keahey K., et al., Science Clouds: Early Experiences in Cloud Computing for Scientific Applications, 2008.

Keyes R., et al., Cloud Computing as a Monte Carlo Cluster for Radiation Therapy, ICCR, 1-4.

Langer S. G., Challenges for Data Storage in Medical Imaging Research, Journal of Digital Imaging, 2011, 203-207, vol. 24, No. 2.

Men C., et al., GPU-based ultrafast IMRT plan optimization, Physics in Medicine and Biology, 2009, 6565-6573, vol. 54.

Owens J. D., et al., A Survey of General-Purpose Computation on Graphics Hardware, The Eurographics Association and Blackwell Publishing LTD., 2007, 80-113, vol. 26, No. 1.

Paganetti H., et al., Clinical Implementation of Full Monte Carlo dose calculation in proton beam therapy, Physics in Medicine and Biology, 2008, 4825-4853, vol. 53.

Philbin J., et al, Will the next generation of PACS be sitting on a cloud?, Journal of Digital Imaging, 2011, 179-183, vol. 24, No. 2.

Purcell T. J., et al., Ray tracing on programmable graphics hardware, ACM Inc., 2002, 703-712.

Rogers D W O., Fifty years of Monte Carlo simulations for medical physics, Physics in Medicine and Biology, 2006, R287-R301, vol. 51.

Sevior M., et al., Belle Monte-Carlo production on the Amazon EC2 cloud, VPAC, 2009, 1-40.

Waters R., How many computers does the world need?, Financial Times Tech Blog, 2009.

Zubal G., et al., Computerized three-dimensional segmented human anatomy, Medical Physics, 1994, 299-302, vol. 21, No. 2.

* cited by examiner

SYSTEM AND METHODS FOR PERFORMING MEDICAL PHYSICS CALCULATIONS

The present application claims priority to U.S. Provisional Patent Application Nos. 61/343,419 filed Apr. 28, 2010 and 61/399,711 filed Jul. 16, 2010, the disclosures of which are hereby incorporated by reference in their entirety.

STATEMENT CONCERNING FEDERALLY SPONSORED RESEARCH

This invention was made with U.S. government support, National Science Foundation CBET 0853157. The U.S. government may have certain rights in the invention.

FIELD OF THE INVENTION

The invention relates generally to cloud computing or utilization of computational resources on demand via a computer network, and particularly to a system and methods for performing medical physics calculations such as energy deposition and radiation fluence. Such calculations may be used in planning radiation therapy treatments, design and quality control of diagnostic medical imaging, and design of radiation shielding, among other applications.

BACKGROUND OF THE INVENTION

Radiation therapy (or radiotherapy) is commonly used in the treatment of various cancers to control the spread of malignant cells. Radiotherapy may be used for curative or adjuvant treatment. When selecting a dose, many other factors are considered by radiation oncologists, including whether the patient is receiving chemotherapy, patient comorbidities, whether radiation therapy is being administered before or after surgery, and the degree of success of surgery. The amount of radiation used in photon radiation therapy varies depending on the type and stage of cancer being treated.

Delivery parameters of a prescribed dose are determined during treatment planning, part of dosimetry. Treatment planning is currently usually performed on dedicated computers using specialized treatment planning software. The planner will try to design a plan that delivers a prescription dose to the tumor and minimizes dose to surrounding healthy tissues. Depending on the radiation delivery method, several angles or sources may be used to sum to the total necessary dose. Proper dosing remains one of the most important considerations of radiation therapy. With proper dosing, ill cells may be targeted and while healthy cells are preserved.

Dosimetric calculations are a crucial component in the accurate delivery and assessment of radiation therapy. As radiation therapy and diagnostics imaging technologies have become more complex, the associated physics calculations have become more resource intensive. These requirements have been largely met by the exponential increase in processor speed and RAM size, but sometimes outstrip the pace of computer technology even for conventional, deterministic calculation techniques. For example, TomoTherapy, Inc.'s TomoHD ships with a 14 node calculation cluster. Non-deterministic algorithms, such as the Monte Carlo method, demand even greater computing resources than conventional algorithms, but generally offer superior dose calculation accuracy. This is particularly true for complex, heterogeneous treatment scenarios such as particle therapy treatment planning. The use of Monte Carlo simulations is highly desirable for dose calculation in radiation therapy as part of treatment planning or verification. In the recent years, Monte Carlo simulations brought the much-needed dosing accuracy to cancer patients. Monte Carlo simulations represent the gold standard in radiation dose calculation since they include the real physics of the interactions of photons with materials.

Notwithstanding its great results, Monte Carlo simulations have not yet been put into routine clinical use due to long calculation times. For example, it has been reported that times of more than 100 CPU hours are required to simulate proton beam treatment plans when using approximately $2 \times 10^7$ primary protons per field. Thus, while Monte Carlo techniques are widely seen as the gold standard of radiation dose calculations, they are only sparingly used clinically in favor of faster, less resource intensive algorithms at the cost of dosimetric accuracy. The primary barrier to widespread adoption of Monte Carlo techniques has been the requirement of large computing resources to achieve clinically relevant run times, particularly in particle therapy applications. These resources, usually in the form of a computing cluster, require a sizable infrastructure investment as well as associated utility, maintenance, upgrades, and personnel costs. These costs make full, analog Monte Carlo methods effectively unfeasible for routine clinical use. This is especially true in particle therapy.

Large-scale, full Monte Carlo simulations and other resource intensive algorithms are often simply considered unfeasible for clinical settings. Very few, if any, clinics are able to use Monte Carlo simulations for routine verifications of their proton therapy plans. Each simulation may take as many as 240 CPU hours for tens of millions of primaries. The majority of the clinical dosimetry systems are based on faster, less resource intensive algorithms, at the cost of dosimetry accuracy.

Cloud computing is a name given to a set of technologies offered as services over the Internet. Pricing is usually based on the pay-as-you-go model, generally billed in hourly increments, and without set contract periods. This scheme allows cloud services to offer on-demand computing infrastructure, sized to fit the user's monetary needs. Cloud computing has become feasible because of the economies of scale afforded by the commoditization of computer hardware, extensive availability of high bandwidth networks, and growth of free, open source software, including operating systems, such as Linux, and virtual machine software.

For clinical usage, cloud computing has many advantages. Cloud resources can be scaled to meet patient and physics quality assurance demand as it fluctuates on a daily basis. Typical computing clusters often face bursts of usage where they are under-utilized most of the day and night and over-queued at peak periods. The cloud paradigm is particularly well suited for one-off calculations, such as machine commissioning and vault shielding calculations, for which a very large cluster might be desirable, but expanding to even a small cluster would be prohibitively expensive for a single run. Also, hardware upgrade and maintenance is taken care of by the provider, rather than by the user.

It would thus be desirable to find a way to improve dosing accuracy, make Monte Carlo calculations more feasible and accessible to clinics and hospitals, and to reduce the costs and computation times associated therewith. Monte Carlo calculations would be particularly well suited to cloud style distributed computing. This is so because the primary particle histories are completely independent of one another, requiring no communication between processes. Monte Carlo calculations, while parallel, need not maintain data or timing synchronization during execution. Until now, however, Monte Carlo calculations in a cloud environment have not been applied to medical physics calculations. Grid computing has been implemented in medical physics calculations, but it is plagued by the same disadvantages as cluster computing. It is inefficient, expensive, and less accessible for medical facilities, despite being widely considered a forerunner to cloud computing.

There is a need to perform medical physics calculations using virtual computer resources versus local dedicated hardware. The present invention satisfies this demand.

SUMMARY OF THE INVENTION

The present invention calculates energy deposition distributions and radiation fluence on a networked virtual computational cluster. Radiation therapy calculations can be performed using a cloud-based, virtual cluster. The systems and methods disclosed herein allow easy, economical and secure access to high performance computing resources for routine clinical applications. What is disclosed is a cloud computing based distributed Monte Carlo dose calculations system and method for implementing Monte Carlo dose calculations for routine clinical use on such systems. Cloud computing fundamentally alters the economics of such calculations by providing relatively cheap, on-demand, pay-as-you-go computing resources over the Internet. Therefore, very large scale Monte Carlo calculations can be routinely performed by clinics and researchers in an efficient and economical way.

The impetus behind using the cloud computing model as a computing cluster is the desire for large scale processing power without an associated large price tag. Costs associated with the cloud are generally only incurred on a usage basis, whereas in-house hardware incurs capital and maintenance costs. Furthermore, additional potential costs in a typical cluster setting involve personnel, utility, equipment housing, insurance, vendor services, and other costs that might be associated with an in-house model. Generally, a typical 100 node cluster would cost $160,000 USD over a 3 year lifetime, when taking into account approximately $1000 USD per node plus $200 USD in maintenance costs per year per node.

The cost of using a cloud-based cluster is primarily determined by the number of CPU-hours used. It is widely accepted in the industry that each patient needs approximately 100 CPU hours of cluster time. Assuming that a typical patient throughput for a clinic is 1000 patients per year, the CPU time necessary would be approximately 100,000 CPU hours. While the rates vary among the different available providers, the average cost is about $0.10 USD per CPU hour, thus costing a typical clinic around $10,000 USD per year. Additional costs may be added for data storage and transfer to and from the cloud. Such additional costs may be around 5% of the annual CPU costs, resulting in a yearly expense of around $10,500—less than 20% of the estimated annual in-house cluster cost. Moreover, these in-house estimates do not take into account the additional expenses incurred for installation and maintenance of cooling systems typically associated with computing clusters and the power consumption of such computing clusters.

A major concern when transferring or storing personal or patient data on networked hardware is the security and privacy of the data. This may even be regulated by the government. But the nature of the calculations discussed herein—radiation dosing—does not require the transfer of full medical records. In fact, very little personal identification information is needed to be sent over a network, and much of the information can be redacted. For example, names can be replaced with hash tags. Moreover, the population has seemingly demonstrated a certain level of comfort and trust in currently available security implementations, as can be seen from the widely accepted use of cloud-based software for PACSn (electronic picture archiving and communication systems) and record storage. Furthermore, while cloud computing is most often associated with CPU-based computing, it can be deployed with a mix of CPU and GPU (graphics processing unit) resources to provide the best possible results. Still further, such a framework can be used with various portals for easy upload of the Monte Carlo calculations. Also, inside the cloud, all virtual nodes may be booted from pre-stored machine images.

In one embodiment, distributions of energy deposition and fluence due to ionizing radiation are determined using a virtual computer cluster over a network such as a distributed processing framework. The distributed processing framework may dynamically monitor the virtual computer cluster, determine the virtual computer cluster size needed for the calculation, and provide the virtual computer cluster of the needed size. Calculation parameters such as Monte Carlo calculation parameters are uploaded and the virtual computer cluster size is determined. The calculation parameters may be uploaded to a cloud computing network. It is contemplated the determination of the virtual computer cluster size needed for the calculation is done at the cloud computing network. Virtual calculation nodes may also be requested from the cloud computing network. The virtual computer cluster size may be dynamic. Calculation tasks are distributed and at least one calculation is performed. Calculation results are combined to obtain a final result that can be returned. The calculation results may occur on a single node or one a plurality of nodes in parallel. The final result may be aggregated linearly or by using a Tree-based distribution model.

The cloud computing paradigm disclosed herein provides new opportunities for medical physics. The framework disclosed herein provides an on-demand, virtual computing cluster running on a commercial cloud computing service. The on-demand nature, ease of access, and pay-as-you-go pricing model yield the promise of providing clinics and researchers access to unprecedented amounts of computing power for medical physics calculations.

The cloud computing approach disclosed herein fundamentally alters the economics of such calculations by providing relatively cheap, on-demand, pay-as-you-go computing resources over the Internet. The invention disclosed herein thus enables very large scale Monte Carlo calculations to be routinely performed by clinics and researchers in an efficient and economical way.

The described embodiments are to be considered in all respects only as illustrative and not restrictive, and the scope of the invention is not limited to the foregoing description. Those of skill in the art will recognize changes, substitutions and other modifications that will nonetheless come within the scope of the invention and range of the claims.

DETAILED DESCRIPTION OF THE PREFERRED EMBODIMENT

As described herein, the preferred embodiments of the present invention provide a method for calculating distributions of energy depositions (or dose) and fluence. Described herein are certain embodiments, however, this does not limit other embodiments from using other suitable methods and materials. Those of skill in the art will appreciate that the following description is related to preferred and/or exemplary embodiments of the present invention. Certain embodiments of the present invention are defined exclusively within the appended claims.

Embodiments of the present invention allow a user to calculate distributions of energy deposition (or dose) and fluence due to ionizing radiation using a virtual, on-demand computing cluster over a network such as the Internet instead of using local, dedicated hardware. Such calculations can be used in planning radiation therapy treatments, design and quality control of diagnostic medical imaging, and design or radiation shielding, among other applications.

Cloud computing is a name given to a set of technologies offered as services over the Internet. Cloud providers such as Google, Inc., Amazon Inc., and Rackspace, Inc. offer computing resources, that is, CPU time, storage, etc., which are scalable to the users' needs. Pricing is usually based on a pay-as-you-go model, generally billed on hourly increments, and without set contract periods. This scheme allows cloud services to offer on-demand computing infrastructure, sized to fit the users' momentary needs. Cloud computing has come about because of the commoditization of computer hardware, extensive availability of high bandwidth networks, and growth of free, open source software, including entire operating systems and virtual machine software.

Figure 1:
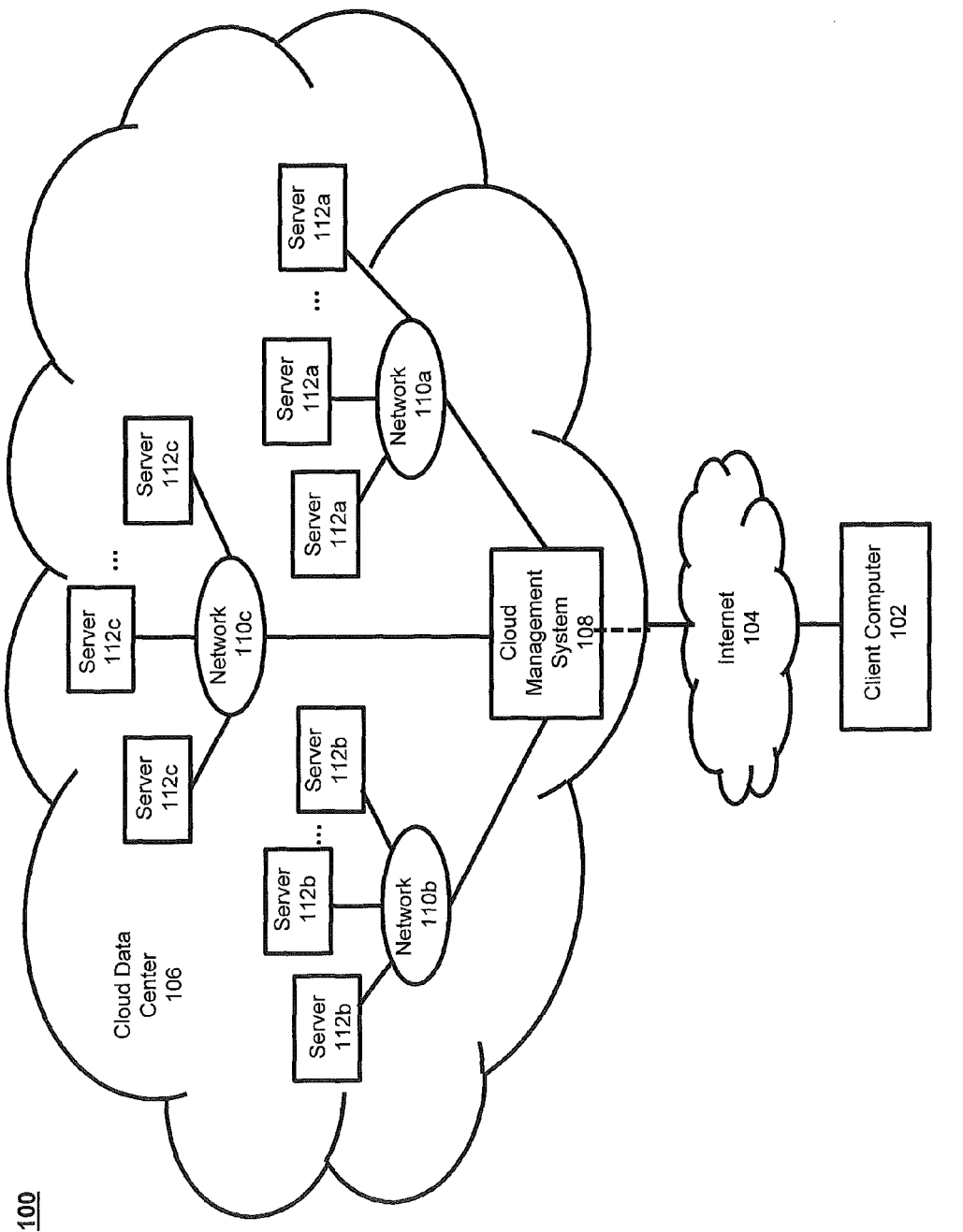
FIG. 1 illustrates an exemplary cloud computing system that may be used to implement the methods according to the present invention.

FIG. 1 illustrates an exemplary cloud computing system 100 that may be used to implement the methods according to the present invention. The cloud computing system 100 includes a plurality of interconnected computing environments. The cloud computing system 100 utilizes the resources from various networks as a collective virtual computer cluster, where the services and applications can run independently from a particular computer or server configuration using virtualization techniques, making hardware less important.

Specifically, the cloud computing system 100 includes at least one client computer 102. The client computer 102 includes memory such as random access memory ("RAM"), read-only memory ("ROM"), mass storage device, or any combination thereof. The memory functions as a computer usable storage medium, otherwise referred to as a computer readable storage medium, to store and/or access computer software and/or instructions.

The client computer 102 also includes a communications interface, for example, a modem, a network interface (such as an Ethernet card), a communications port, a PCMCIA slot and card, wired or wireless systems, etc. The communications interface allows communication through transferred signals between the client computer 102 and external devices including networks such as the Internet 104 and cloud data center 106. Communication may be implemented using wireless or wired capability such as cable, fiber optics, a phone line, a cellular phone link, radio waves or other communication channels.

The client computer 102 establishes communication with the Internet 104—specifically to one or more servers—to, in turn, establish communication with one or more cloud data centers 106. A cloud data center 106 includes one or more networks 110a, 110b, 110c managed through a cloud management system 108. Each network 110a, 110b, 110c includes resource servers 112a, 112b, 112c, respectively. Servers 112a, 112b, 112c permit access to a collection of computing resources and components that can be invoked to instantiate a virtual machine, process, or other resource for a limited or defined duration. For example, one group of resource servers can host and serve an operating system or components thereof to deliver and instantiate a virtual machine. Another group of resource servers can accept requests to host computing cycles or processor time, to supply a defined level of processing power for a virtual machine. A further group of resource servers can host and serve applications to load on an instantiation of a virtual machine, such as an email client, a browser application, a messaging application, a calculations application or other applications or software.

The cloud management system 108 can comprise a dedicated or centralized server and/or other software, hardware, and network tools to communicate with one or more networks 110a, 110b, 110c, such as the Internet or other public or private network, with all sets of resource servers 112a, 112b, 112c. The cloud management system 108 may be configured to query and identify the computing resources and components managed by the set of resource servers 112a, 112b, 112c needed and available for use in the cloud data center 106. Specifically, the cloud management system 108 may be configured to identify the hardware resources and components such as type and amount of processing power, type and amount of memory, type and amount of storage, type and amount of network bandwidth and the like, of the set of resource servers 112a, 112b, 112c needed and available for use in the cloud data center 106. Likewise, the cloud management system 108 can be configured to identify the software resources and components, such as type of Operating System ("OS"), application programs, and the like, of the set of resource servers 112a, 112b, 112c needed and available for use in the cloud data center 106.

The cloud computing system 100 of FIG. 1 is provided only for purposes of illustration and does not limit the invention to this specific embodiment. It is appreciated that a person skilled in the relevant art knows how to program and implement the invention using any computer system or network architecture.

Figure 2:
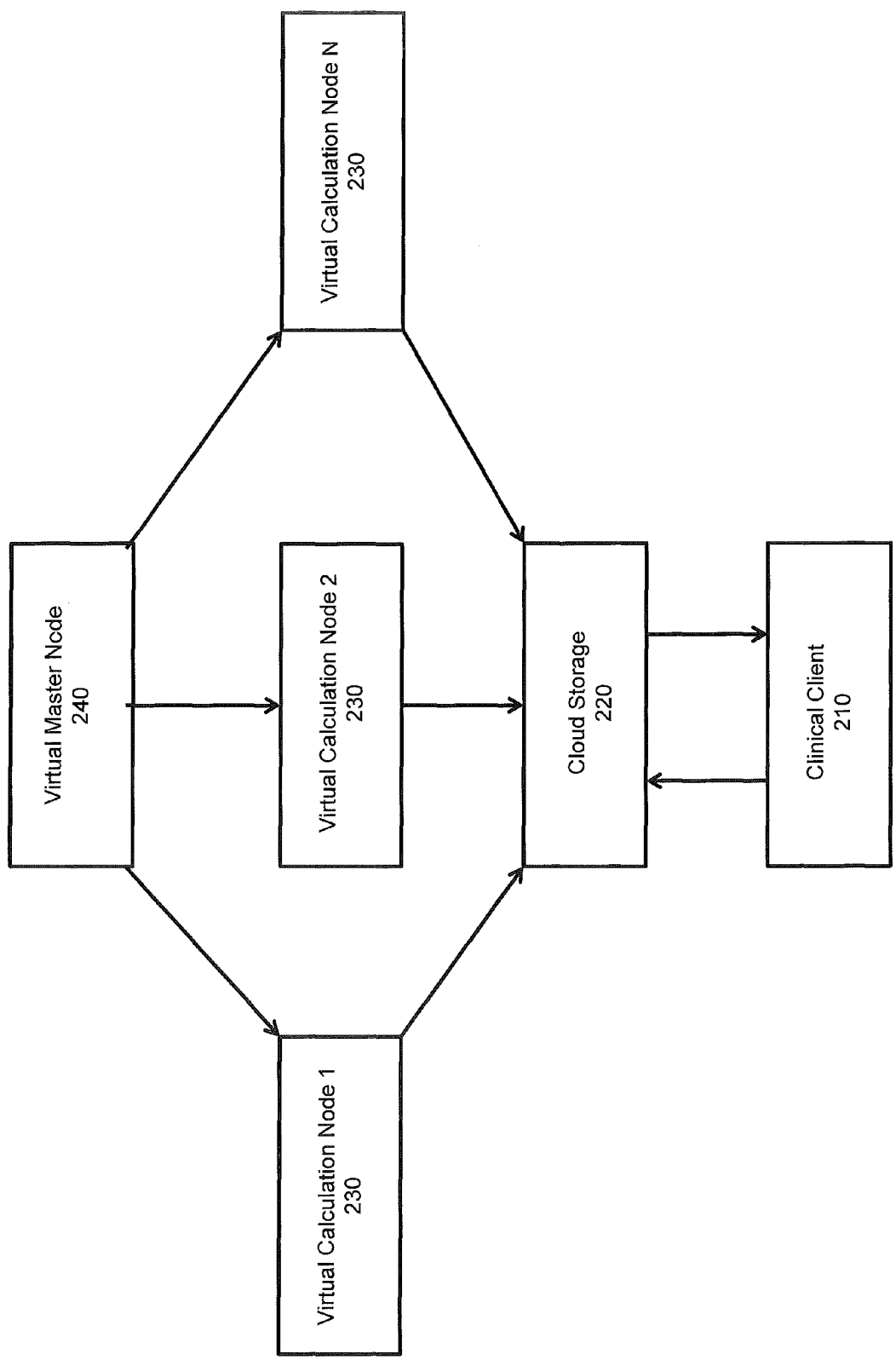
FIG. 2 is a diagram of a general scheme for calculating doses using the cloud paradigm according to the present invention.

An embodiment of the process disclosed herein relies on a cloud computing model of virtual computer resources depicted in FIG. 2. Calculations parameters or input files are uploaded or otherwise sent from a local client computer 210 over a network to a remote network data storage, such as the cloud storage 220 and virtual calculation nodes are requested. Additional parameters, such as time requirements, may be sent from the local client computer 210 to specify the number of virtual calculation nodes 230 to instantiate for the calculations. If virtual nodes 230 are already running from a previous calculation, a master node 240 can start additional virtual nodes 230 or reduce the number as necessary. The dose calculation engines will be running on each virtual node as well. There can be one or more master nodes 240 in the network. The calculation parameters can be retrieved from the network data storage 220 and calculation tasks can then be distributed among the virtual nodes 230 by the master node 240. The master node 240 can also keep a list of the network addresses of all virtual nodes 230 in order to monitor the progress of calculations, restart processes as necessary, begin the combination and return steps, and finally terminate the virtual nodes 230 if necessary. The input file is distributed to each node, given a unique, random seed, and a Monte Carlo or other calculation is carried out. The calculations can be performed with a dose calculation engine residing on the virtual nodes. Once the calculations on the individual virtual nodes 230 have been completed and stored in files, data streams or data objects, the results can be combined. The combination process can take place on the virtual nodes 230 or on the local client 210. Alternatively, the result combination can occur on a single master node or in parallel. If the results are combined on a virtual node 230, the results can be combined by any number of virtual nodes before the final result is passed to the network storage 220 and back to the local client 210. The results are aggregated using a linear model or a tree-based distributive model, and a final dose distribution is returned to the user. Finally, the master node 240 resets the virtual nodes 230 to wait for the next calculation or terminate them if no further calculations are to be performed.

By way of example, such medical physics calculations can be performed through a number of different cloud computing providers. They can be carried out on Amazon Web Service's (AWS) Elastic Compute Cloud (EC2). Several other vendors offer similar cloud services. AWS's EC2 offers several different processor-RAM combinations at different hourly rates. A virtual appliance can be used to instantiate or create a virtual machine within a cloud. To the user, this process is just like booting up a standard server computer. Once the instance is up and running, it will have a unique IP address and a domain name, allowing the user to log in. A virtual cluster can be built by requesting multiple virtual nodes (instances). The size of the cluster can be scaled on demand, that is, virtual nodes can be dynamically created and destroyed. Files can be stored on the running virtual nodes as well as on the persistent storage server at the chosen cloud computing provider to facilitate transfer to and from the cloud. From a user perspective, the persistent storage service can be viewed as the counterpart of the underlying network file system (NFS) found in most cluster computing environments.

Figure 3:
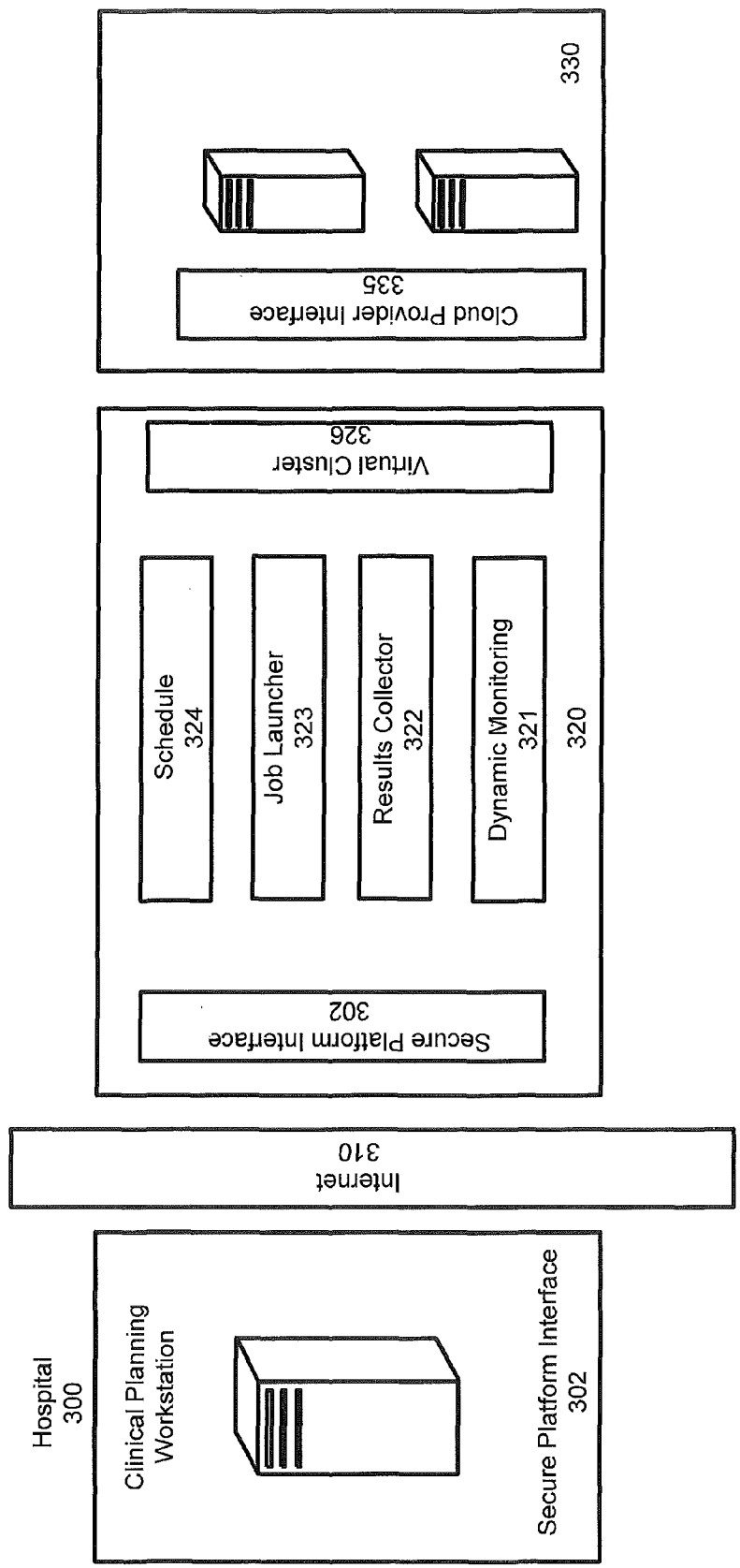
FIG. 3 is a diagram of a system for calculating doses incorporating a distributed processing framework according to the present invention.
Figure 4:
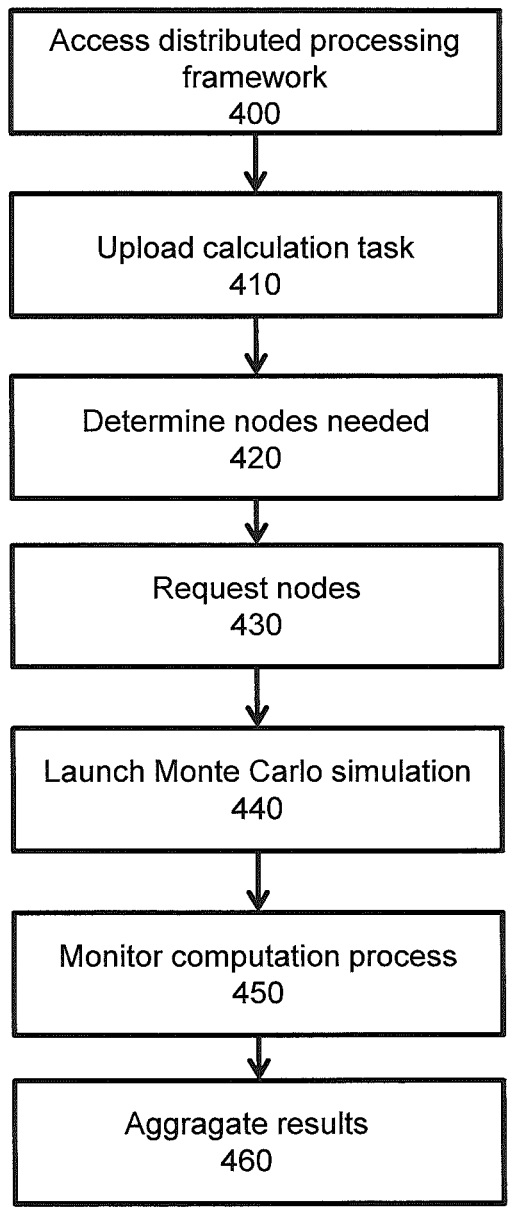
FIG. 4 is a flowchart of a method of calculating doses using a cloud paradigm incorporating a distributed processing framework according to the present invention.

According to another exemplary embodiment, a custom distributed processing framework can additionally be implemented to access the chosen cloud computing provider and the secure shell protocol (SSH) for network communications. Such a distributed processing framework can be viewed as a bridge between the clinics and commercial cloud computing providers. Hospitals and clinics can interact with the distributed processing framework through a custom designed platform interface. The distributed processing framework can host such functions as keeping track of the available nodes in a virtual cluster, launching the requisite number of nodes by, dynamically monitoring the size of the cluster, and collecting computation results. As such, at any moment, the distributed processing framework can maintain a virtual cluster and dynamically monitor the health of the cluster. For example, if some nodes failed, it would immediately request replacements from the cloud; if system load were low, it would dynamically reduce the size of the cluster. The use of the virtual nodes and other computing resources can be administered by a scheduling function residing on the distributed processing framework. The scheduling function helps to keep track of the available nodes in the virtual cluster. The job launching function determines the number of nodes needed for the computation based on the time constraints, the anatomy and the number of particles to be simulated and request the appropriate number of nodes from the scheduling function. Since nodes may fail, redundancy is preferably incorporated. For example, instead of requesting n number of nodes for the computation, the job launching function may request 5% more nodes, or some threshold based on reliability statistics. The results collecting function will collect the results from the virtual calculation nodes The general data flow of the cloud based calculations incorporating the distributed processing framework is discussed in detail with reference to FIG. 3 and FIG. 4 and is as follows. At step 400, a user at a hospital or clinic 300 accesses a distributed processing framework 320 through a secure platform interface 302. The distributed processing framework 320 can be viewed as a bridge between the hospital or clinic 300 and commercial cloud computing provider 330. Generally speaking, the distributed processing framework may have two components. One component is installed in the hospital or clinical facilities 300, while the other component is installed in the cloud 330. Hospital or clinic 300 may interact with the distributed processing framework 320 through a custom designed platform interface 302. At any moment, distributed processing framework 320 may maintain a virtual cluster of tens to thousands of nodes and dynamically monitor the health of the cluster.

A Monte Carlo calculation task (including patient anatomy, beam configuration, etc.) is uploaded onto the distributed processing framework 320 using the secure platform interface 302 via the Internet 310 at step 410. At step 420 the job launching function 323 determines the number of nodes needed for the computation based on the time-constraint, the anatomy and the number of primaries needed. At step 430 the job launching function requests the appropriate number of nodes from the scheduling function 324. Since the nodes may fail, redundancy may be incorporated. At step 440 the Monte Carlo simulation is launched on each requested node in a distributive manner. Extra care is used for random seed generations to ensure the correctness of the simulations. At step 450 the progress of the computation is dynamically monitored. Since nodes may fail during the computation, success is declared once the number of nodes that completes the computation reaches a certain threshold, for example 95% of nodes. The cloud provider interface 335 may be in communication with the distributed processing framework 320.

Once the computation is finished on each of the virtual nodes, the results are aggregated at step 460 using a linear model or a tree-based distributive model, and a final dose distribution is returned to the user.

Figure 5:
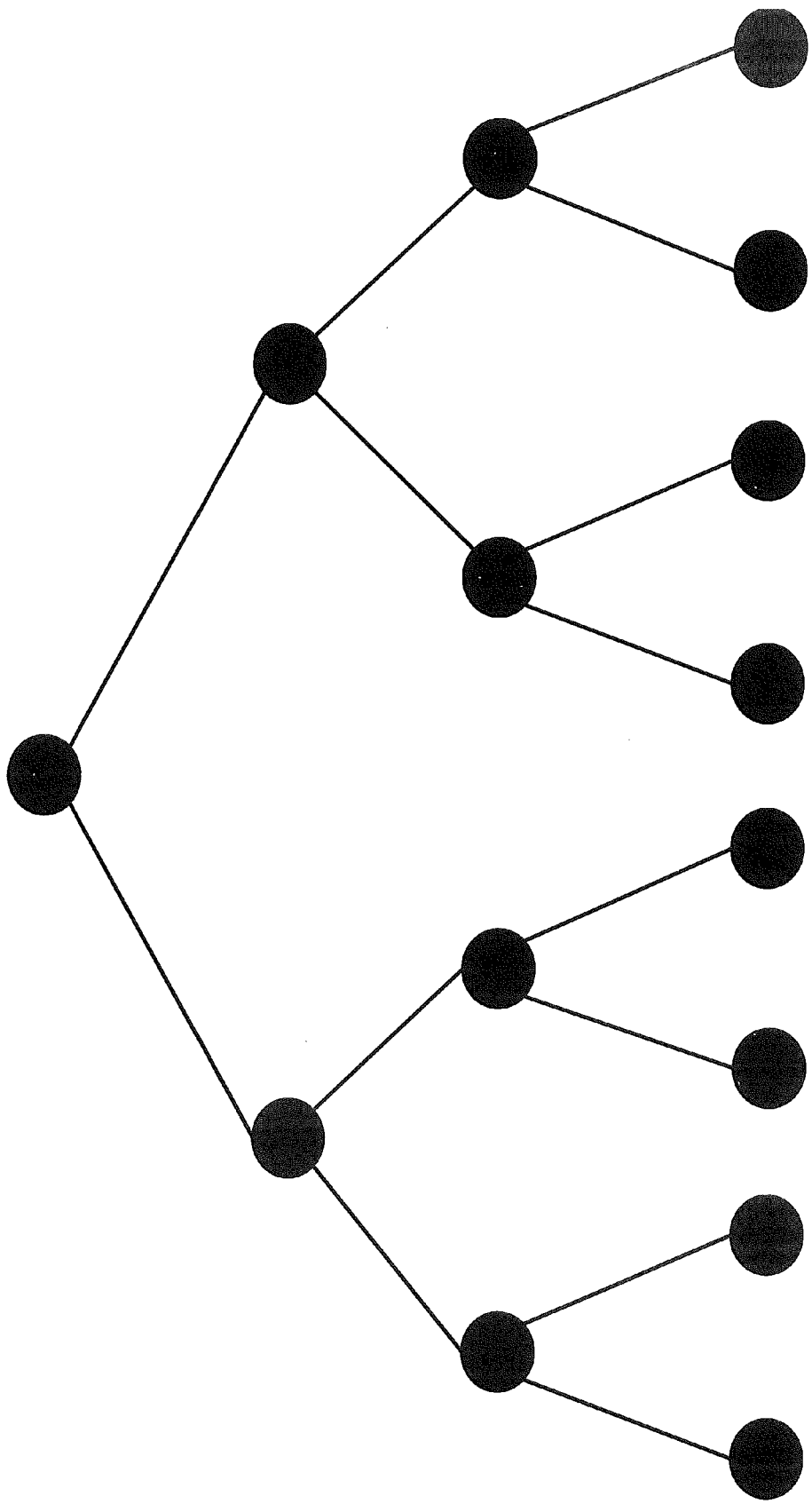
FIG. 5 illustrates results aggregation using a tree-based overlay framework according to the present invention.

FIG. 5 illustrates results aggregation using a tree-based overlay framework, where a tree topology is imposed on the nodes requested and can reduce data aggregation to $\log_d n$ rounds of computation, where d is the fan out of each node. As an example, in FIG. 5, there are a total of 15 nodes in the cluster, a linear aggregation will take 14 rounds of computation, while using a binary tree topology (d=2) will reduce the computation to 4 rounds ($\approx \log_2 15$).

The invention claimed is:

1. A method of determining distributions of energy deposition and fluence due to ionizing radiation comprising the steps of:
providing a client computer and a network, wherein the network includes a data storage, a virtual computer cluster comprising a plurality of nodes and a master node;
uploading Monte Carlo calculation parameters by the client computer to the data storage of the network, wherein the Monte Carlo calculation parameters consisting essentially of a patient anatomy, a time constraint, and a beam configuration for determining distributions of energy deposition and fluence due to ionizing radiation;
using two or more of the Monte Carlo calculation parameters to determine by the master node a number of nodes needed to complete Monte Carlo calculations to define a virtual computer cluster, wherein the number of nodes determined by the master node to define a virtual computer cluster includes a number of additional nodes, the number of additional nodes determined by a threshold amount;
retrieving by the master node the Monte Carlo calculation parameters;
distributing by the master node to each node of the virtual computer cluster one or more Monte Carlo calculation parameters;
using the Monte Carlo calculation parameters to perform by each node of the virtual computer cluster at least one Monte Carlo calculation to compute a dose calculation result;
combining by the master node the dose calculation result from each node of the virtual computer cluster to calculate a final dose calculation result, wherein said combining step further includes the step of using a tree-based distribution model to obtain the final result, said combining step performed when the number of nodes of the virtual computer cluster that completes the computation of the dose calculation result meets a threshold value; and
returning by the master node to the client computer the final dose calculation result.

2. The method of claim 1, wherein the size of the virtual computer clusters is dynamic.

3. The method of claim 1, wherein the combining step further includes the step of aggregating linearly the result from each node of the virtual computer cluster.

4. The method of claim 1, wherein the number of nodes equals one.

5. The method of claim 1 further comprising the step of monitoring dynamically the virtual computer cluster.

6. The method of claim 1, wherein the network is a cloud computing network.

7. The method of claim 1, wherein the final dose calculation result is a dose distribution.

8. The method of claim 7, wherein the dose distribution is one or more quantities including physical energy absorbed per unit mass and linear energy transfer (LET).

9. The method of claim 7 further comprising the step of storing the final dose calculation result in the data storage of the network.

10. The method of claim 7 further comprising the steps of:
storing by the master node a list of network addresses for each node; and
monitoring progress of the at least one Monte Carlo calculation performed by each node of the virtual computer cluster.

11. The method of claim 1, wherein the threshold value is 95%.

12. The method of claim 1, wherein the tree-based distribution model reduces data aggregation to $\log_d n$, where d is the tree topology and n is the number of nodes.

13. The method of claim 12, wherein the tree topology is a binary tree topology (d=2).

14. The method of claim 1, wherein the threshold amount is 5%.

* * * * *